United States Patent
Guevremont et al.

(10) Patent No.: US 7,250,306 B2
(45) Date of Patent: Jul. 31, 2007

(54) METHOD FOR DISTINGUISHING BETWEEN PROTEIN VARIANTS

(75) Inventors: Roger Guevremont, Ottawa (CA); Randy Purves, Orleans (CA)

(73) Assignee: Thermo Finnigan LLC, San Jose, CA (US)

( * ) Notice: Subject to any disclaimer, the term of this patent is extended or adjusted under 35 U.S.C. 154(b) by 541 days.

(21) Appl. No.: 10/359,576

(22) Filed: Feb. 7, 2003

(65) Prior Publication Data

US 2003/0153087 A1    Aug. 14, 2003

Related U.S. Application Data

(60) Provisional application No. 60/354,711, filed on Feb. 8, 2002.

(51) Int. Cl.
*G01H 24/00* (2006.01)
*G01H 31/00* (2006.01)

(52) U.S. Cl. ........................................ 436/173; 436/15

(58) Field of Classification Search ...................... None
See application file for complete search history.

(56) References Cited

U.S. PATENT DOCUMENTS

| | | | |
|---|---|---|---|
| 5,420,424 A | 5/1995 | Carnahan et al. | |
| 5,905,258 A | 5/1999 | Clemmer et al. | |
| 6,504,149 B2 | 1/2003 | Guevremont et al. | |
| 6,621,077 B1 | 9/2003 | Guevremont et al. | |
| 6,639,212 B1 | 10/2003 | Guevremont et al. | |

FOREIGN PATENT DOCUMENTS

| | | |
|---|---|---|
| WO | WO 97/49993 A1 | 12/1997 |
| WO | WO 00/08454 A1 | 2/2000 |
| WO | WO 02/08767 A2 | 1/2002 |

OTHER PUBLICATIONS

Srebalus et al. "Determining synthetic failures in combinatorial libraries by hybrid gas-phase separation methods", Journal of the American Society for Mass Spectrometry (2000), 11(4), 352-355.*

(Continued)

*Primary Examiner*—Yelena G. Gakh
(74) *Attorney, Agent, or Firm*—Freedman & Associates

(57) ABSTRACT

Disclosed is a method for distinguishing between protein variants using high field asymmetric waveform ion mobility spectrometry (FAIMS). A method according to the instant invention includes the steps of providing a FAIMS analyzer region defined by a space between two spaced-apart electrodes, and providing predetermined conditions within said FAIMS analyzer region. Ions of an analyte protein are produced from a solution having predetermined properties and including the analyte protein, using a suitable ionization source. The ions are introduced into the FAIMS analyzer region, transmitted therethrough, and detected. An intensity of the detected ions is measured at a predetermined CV value. At least a difference is determined, between the detected intensity and a reference value, the reference value relating to an expected intensity at the predetermined CV value for a reference form of the analyte protein. The analyte protein is registered as a variant of the reference form, in dependence upon the determined differences.

16 Claims, 9 Drawing Sheets

OTHER PUBLICATIONS

Mohimen et al. "A chemometric approach to detection and characterization of multiple protein conformers in solution using eletrospray ionization mass spectrometry", Anal. Chem., 2003, v. 75, pp. 4139-4147.*

Ogorzalek Loo et al. "Protein transfer reaction studies of multiply charged proteoins in a high mass-to-charge ratio quadrupole mass spectrometer", J. Am. Soc. Mass Spectrom., 1994, v. 5, pp. 1064-1071.*

Hudgins et al., "High Resolution Ion Mobility Measurements for Gas Phase Proteins: Correlation Between Solution Phase and Gas Phase Conformations", Int'l Journal of Mass Spectrometry and Ion Processes, Elsevier Scientific Publishing Co., Amsterdam NL, vol. 165-166, pp. 497-507, XP004103206, Nov. 1, 1997.

Purves et al., "Separation of Protein Conformers Using Electrospray-High Field Asymmetric Waveform Ion Mobility Spectrometry-Mass Spectrometry" Int'l Journal of Mass Spectrometry, Elsevier Science Publishers, Amsterdam NL, vol. 197, No. 1-3, pp. 163-177, XP004190811, Feb. 2002.

Carr et al., "Plasma Chromatography", Plenum Press (1984), NY, USA.

Mason et al., "Transport Properties of Ions in Gases", Wiley (1988), NY, USA.

Buryakov et al., "A New Method of Separation of Multi-Atomic Ions by Mobility at Atmospheric Pressure using a High-Frequency Amplitude-Asymmetric Strong Electric Field", Int. J. Mass Spectrom. Ion Processes, No. 128, pp. 143-148, Elsevier Science Publishers B.V. (1993).

Covey et al., "Collision Cross Sections for Protein Ions", Journal of the American Society for Mass Spectrometry, 4, pp. 1-8 (1993).

Cox et al., "Conformer Selection of Protein Ions by Ion Mobility in a Triple Quadrupole Mass Spectrometer", Journal of the American Society for Mass Spectrometry, 5, pp. 127-136 (1994).

Eiceman et al., "Ion Mobility Spectrometry", (1994), CRC Press, FL, USA.

Carnahan et al., "Field Ion Spectrometry—A New Analytical Technology for Trace Gas Analysis", Proceedings of the 41st Annual ISA Analysis Division Symposium, paper #96-009, pp. 87-95, (1996), Framingham, MA, USA.

Collings et al., "Conformation of Gas-Phase Myoglobin Ions", J. Am. Chem. Soc., vol. 118, No. 18, pp. 4488-4489 (1996).

Riegner et al., "Qualitative Evaluation of Field Ion Spectrometry for Chemical Warfare Agent Detection", Proceedings of the 45th ASMS Conference on Mass Spectrometry and Allied Topics, pp. 473, (1997), Palm Springs, CA, USA.

Guevremont et al., "Combined Ion Mobility/Time-of-Flight Mass Spectrometry Study of Electrospray-Generated Ions", Analytical Chemistry, vol. 69, No. 19, pp. 3959-3965, (1997).

Hudgins et al., "High Resolution Ion Mobility Measurements for Gas Phase Proteins: Correlation between Solution Phase and Gas Phase Conformations", International. Journal of Mass Spectrometry and Ion Processes, 165/166, pp. 497-507, Elsevier Science B.V. (1997).

Henderson et al., "ESI/Ion Trap/Ion Mobility/time-of-Flight Mass Spectrometry for Rapid and Sensitive Analysis of Biomolecular Mixtures", Analytical Chemistry, vol. 71, No. 2, pp. 291-301, American Chemical Society (1999).

Krulov, "A Method of Reducing Diffusion Losses in a Drift Spectrometer", Tech. Phys., vol. 44, No. 1, pp. 113-116, American Institute of Physics (1999).

Guevremont et al., "High Field Asymmetric Waveform Ion Mobility Spectrometry-Mass Spectrometry: an Investigation of Leucine Enkephalin Ions Produced by Electrospray Ionization", Journal of the American Society for Mass Spectrometry, v. 10, p492-501, (1999).

Spangler, "Fundamental Considerations for the Application of Miniature Ion Mobility Spectrometry to Field Analytical Applications", Field Analytical Chemistry and Technology, 4, pp. 255-267 (2000), USA.

Eiceman et al., "Monitoring Volatile Organic Compounds in Ambient Air Anside and Outside Buildings with the use of a Radio-Frequency-Based Ion-Mobility Analyzer with a Micromachined Drift Tube", Field Analytical Chemistry and Technology, 4, pp. 297-308 (2000), USA.

Miller et al., "A Novel Micromachined High-Field Asymmetric Waveform-Ion Mobility Spectrometer", Sensors and Actuators B Chemical, 67, pp. 300-306, Elsevier Science S.A. (2000).

Purves et al., "Investigation of Bovine Ubiquitin Conformers Separated by High-Field Asymmetric Waveform Ion Mobility Spectrometry: Cross Sections Meausrements Using Enery-Loss Experiments with a Triple Quadrupole Mass Spectrometer", Journal of the American Society for Mass Spectrometry, vol. 11, pp. 738-745, (2000).

Guevremont et al., "Analysis of a tryptic digest of pig hemoglobin using ESI-FAIMS-MS", Analytical Chemistry, vol. 72, pp. 4577-4584, American Chemical Society, (2000).

Miller et al., "A MEMS Radio-Frequency Ion Mobility Spectrometer for Chemical Vapor Detection", Sensors and Actuators A Physical, 91, pp. 307-318, Elsevier Science S.A. (2000).

Eiceman et al., "Miniature Radio-Frequency Mobility Analyzer as a Gas Chromatographic Detector for Oxygen-Containing Volatile Organic Compounds, Pheromones and other Insect Attractants", Journal of Chromatography A, 917, pp. 205-217, Elsevier Science B.V. (2001).

Buryakov et al., "Detection of Explosive Vapors in the Air Using an Ion Drift Nonlinearity Spectrometer", Journal of Analytical Chemistry, vol. 56, No. 4, pp. 336-340 (2001).

Purves et al., "Elongated Conformers of Charge States +11 to +15 of Bovine Ubiquitin Studied Using ESI-FAIMS-MS", Journal of the American Society for Mass Spectrometry, vol. 12, pp. 894-901, Elsevier Science Inc. (2001).

Spangler et al., "Application of Mobility Theory to the Interpretation of Data Generated by Linear and RF Excited Ion Mobility Spectrometers", International Journal of Mass Spectrometry, 12017, pp. 1-10, Elsevier Science B.V. (2002).

* cited by examiner

METHOD FOR DISTINGUISHING BETWEEN PROTEIN VARIANTS

This application claims the benefit of U.S. Provisional Application No. 60/354,711 filed Feb. 8, 2002.

FIELD OF THE INVENTION

The instant invention relates generally to high field asymmetric waveform ion mobility spectrometry (FAIMS), more particularly the instant invention relates to a method for distinguishing between protein variants using FAIMS.

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are separated in the drift tube on the basis of differences in their drift velocities. At low electric field strength, for example 200 V/cm, the drift velocity of an ion is proportional to the applied electric field strength and the mobility, K, which is determined from experimentation, is independent of the applied electric field. Additionally, in IMS the ions travel through a bath gas that is at sufficiently high pressure that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, N.Y., 1988) teach that at high electric field strength, for instance fields stronger than approximately 5,000 V/cm, the ion drift velocity is no longer directly proportional to the applied electric field, and K is better represented by $K_H$, a non-constant high field mobility term. The dependence of $K_H$ on the applied electric field has been the basis for the development of high field asymmetric waveform ion mobility spectrometry (FAIMS). Ions are separated in FAIMS on the basis of a difference in the mobility of an ion at high field strength, $K_H$, relative to the mobility of the ion at low field strength, K. In other words, the ions are separated due to the compound dependent behavior of $K_H$ as a function of the applied electric field strength.

In general, a device for separating ions according to the FAIMS principle has an analyzer region that is defined by a space between first and second spaced-apart electrodes. The first electrode is maintained at a selected dc voltage, often at ground potential, while the second electrode has an asymmetric waveform V(t) applied to it. The asymmetric waveform V(t) is composed of a repeating pattern including a high voltage component, $V_H$, lasting for a short period of time $t_H$ and a lower voltage component, $V_L$, of opposite polarity, lasting a longer period of time $t_L$. The waveform is synthesized such that the integrated voltage-time product, and thus the field-time product, applied to the second electrode during each complete cycle of the waveform is zero, for instance $V_H t_H + V_L t_L = 0$; for example +2000 V for 10 μs followed by −1000 V for 20 μs. The peak voltage during the shorter, high voltage portion of the waveform is called the "dispersion voltage" or DV, which is identically referred to as the applied asymmetric waveform voltage.

Generally, the ions that are to be separated are entrained in a stream of gas flowing through the FAIMS analyzer region, for example between a pair of horizontally oriented, spaced-apart electrodes. Accordingly, the net motion of an ion within the analyzer region is the sum of a horizontal x-axis component due to the stream of gas and a transverse y-axis component due to the applied electric field. During the high voltage portion of the waveform an ion moves with a y-axis velocity component given by $V_H = K_H E_H$, where $E_H$ is the applied field, and $K_H$ is the high field ion mobility under operating electric field, pressure and temperature conditions. The distance traveled by the ion during the high voltage portion of the waveform is given by $d_H = v_H t_H = K_H E_H t_H$, where $t_H$ is the time period of the applied high voltage. During the longer duration, opposite polarity, low voltage portion of the asymmetric waveform, the y-axis velocity component of the ion is $v_L = KE_L$, where K is the low field ion mobility under operating pressure and temperature conditions. The distance traveled is $d_L = V_L t_L = KE_L t_L$. Since the asymmetric waveform ensures that $(V_H t_H) + (V_L t_L) = 0$, the field-time products $E_H t_H$ and $E_L t_L$ are equal in magnitude. Thus, if $K_H$ and K are identical, $d_H$ and $d_L$ are equal, and the ion is returned to its original position along the y-axis during the negative cycle of the waveform. If at $E_H$ the mobility $K_H > K$, the ion experiences a net displacement from its original position along the y-axis. For example, if a positive ion travels farther during the positive portion of the waveform, for instance $d_H > d_L$, then the ion migrates away from the second electrode and eventually will be neutralized at the first electrode.

In order to reverse the transverse drift of the positive ion in the above example, a constant negative dc voltage is applied to the second electrode. The difference between the dc voltage that is applied to the first electrode and the dc voltage that is applied to the second electrode is called the "compensation voltage" (CV). The CV voltage prevents the ion from migrating toward either the second or the first electrode. If ions derived from two compounds respond differently to the applied high strength electric fields, the ratio of $K_H$ to K may be different for each compound. Consequently, the magnitude of the CV that is necessary to prevent the drift of the ion toward either electrode is also different for each compound. Thus, when a mixture including several species of ions, each with a unique $K_H/K$ ratio, is being analyzed by FAIMS, only one species of ion is selectively transmitted to a detector for a given combination of CV and DV. In one type of FAIMS experiment, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained.

U.S. Pat. No. 5,420,424, issued to Carnahan and Tarassov on May 30 1995, teaches a FAIMS device having cylindrical electrode geometry and electrometric ion detection, the contents of which are incorporated herein by reference. The FAIMS analyzer region is defined by an annular space between inner and outer cylindrical electrodes. In use, ions that are to be separated are entrained into a flow of a carrier gas and are carried into the analyzer region via an ion inlet orifice. Once inside the analyzer region, the ions become distributed all the way around the inner electrode as a result of the carrier gas flow and ion-ion repulsive forces. The ions are selectively transmitted within the analyzer region to an ion extraction region at an end of the analyzer region opposite the ion inlet end. In particular, a plurality of ion outlet orifices is provided around the circumference of the outer electrode for extracting the selectively transmitted ions from the ion extraction region for electrometric detection. Of course, the electrometric detectors provide a signal that is indicative of the total ion current arriving at the detector. Accordingly, the CV spectrum that is obtained using the Carnahan device does not include information relating to an identity of the selectively transmitted ions. It is a limitation of the Carnahan device that the peaks in the CV spectrum are highly susceptible to being assigned incorrectly.

Replacing the electrometric detector with a mass spectrometer detection system provides an opportunity to obtain additional experimental data relating to the identity of ions giving rise to the peaks in a CV spectrum. For instance, the mass-to-charge (m/z) ratio of ions that are selectively transmitted through the FAIMS at a particular combination of CV and DV can be measured. Additionally, replacing the mass spectrometer with a tandem mass spectrometer makes it possible to perform a full-fledged structural investigation of the selectively transmitted ions. Unfortunately, the selectively transmitted ions are difficult to extract from the analyzer region of the Carnahan device for subsequent detection by a mass spectrometer. In particular, the orifice plate of a mass spectrometer typically includes a single small sampling orifice for receiving ions for introduction into the mass spectrometer. This restriction is due to the fact that a mass spectrometer operates, at a much lower pressure than the FAIMS analyzer. In general, the size of the sampling orifice into the mass spectrometer is limited by the pumping efficiency of the mass spectrometer vacuum system. In principle, it is possible to align the sampling orifice of a mass spectrometer with a single opening in the FAIMS outer electrode of the Carnahan device; however, such a combination suffers from very low ion transmission efficiency and therefore poor detection limits. In particular, the Carnahan device does not allow the selectively transmitted ions to be concentrated for extraction through the single opening. Accordingly, only a small fraction of the selectively transmitted ions are extracted from the analyzer region, the vast majority of the selectively transmitted ions being neutralized eventually upon impact with an electrode surface.

Guevremont et al. describe the use of curved electrode bodies, for instance inner and outer cylindrical electrodes, for producing a two-dimensional atmospheric pressure ion focusing effect that results in higher ion transmission efficiencies than can be obtained using, for example, a FAIMS device having parallel plate electrodes. In particular, with the application of an appropriate combination of DV and CV an ion of interest is focused into a band-like region between the cylindrical electrodes as a result of the electric fields which change with radial distance. Focusing the ions of interest has the effect of reducing the number of ions of interest that are lost as a result of the ion suffering a collision with one of the inner and outer electrodes.

In WO 00/08455, the contents of which are incorporated herein by reference, Guevremont and Purves describe an improved tandem FAIMS/MS device, including a domed-FAIMS analyzer. In particular, the domed-FAIMS analyzer includes a cylindrical inner electrode having a curved surface terminus proximate the ion outlet orifice of the FAIMS analyzer region. The curved surface terminus is substantially continuous with the cylindrical shape of the inner electrode and is aligned co-axially with the ion outlet orifice. During use, the application of an asymmetric waveform to the inner electrode results in the normal ion-focusing behavior as described above, except that the ion-focusing action extends around the generally spherically shaped terminus of the inner electrode. This causes the selectively transmitted ions to be directed generally radially inwardly within the region that is proximate the terminus of the inner electrode. Several contradictory forces are acting on the ions in this region near the terminus of the inner electrode. The force of the carrier gas flow tends to influence the ion cloud to travel towards the ion-outlet orifice, which advantageously also prevents the ions from migrating in a reverse direction, back towards the ionization source. Additionally, the ions that get too close to the inner electrode are pushed back away from the inner electrode, and those near the outer electrode migrate back towards the inner electrode, due to the focusing action of the applied electric fields. When all forces acting upon the ions are balanced, the ions are effectively captured in every direction, either by forces of the flowing gas, or by the focusing effect of the electric fields of the FAIMS mechanism. This is an example of a three-dimensional atmospheric pressure ion trap, as described in greater detail by Guevremont and Purves in WO 00/08457, the contents of which are incorporated herein by reference.

Guevremont and Purves further disclose a near-trapping mode of operation for the above-mentioned tandem FAIMS/MS device, which achieves ion transmission from the domed-FAIMS to a mass spectrometer with high efficiency. Under near-trapping conditions, the ions that accumulate in the three-dimensional region of space near the spherical terminus of the inner electrode are caused to leak from this region, being pulled by a flow of gas towards the ion-outlet orifice. The ions that leak out from this region do so as a narrow, approximately collimated beam, which is pulled by the gas flow through the ion-outlet orifice and into a smaller orifice leading into the vacuum system of the mass spectrometer. Accordingly, such tandem FAIMS/MS devices are highly sensitive instruments that are capable of detecting and identifying ions of interest at part-per-billion levels.

Currently, there is a very limited amount of prior art knowledge relating to the use of FAIMS for studying protein ions in the gas phase. Unlike the majority of ions that have been the subject of early FAIMS studies, protein ions can adopt a plurality of different 3-dimensional structures, or conformations, depending upon several factors including the pH, temperature and composition including salt concentration, of the solution containing the protein. In general, the function of a protein in a living organism is very specific to its 3-dimensional structure in solution. In WO 00/08454, now U.S. Pat. No. 6,639,212 the contents of which are incorporated herein by reference, Guevremont et al. describe the separation of gas-phase protein conformers using a FAIMS apparatus. It was demonstrated that multiple gas-phase conformers of the protein bovine ubiquitin are uniquely detectable using FAIMS. The ability to detect the different multiple conformers of a protein ion results in a CV spectrum containing multiple peaks, having different relative intensities, at unique CV values. Of course, in U.S. Pat. No. 6,639,212 Guevremont et al. examined the effect of experimental conditions on the 3-dimensional structures of protein ions having a same primary sequence of amino acids. In particular, each of a plurality of experimental conditions was systematically varied so as to selectively favor some of the different 3-dimensional structures over other different 3-dimensional structures of a same type of protein.

However, it is also known that the 3-dimensional structure of a protein is very sensitive to modifications to its primary sequence of amino acids. For example, sickle cell anemia in humans results from a single change in the primary sequence of the beta chain of hemoglobin, which includes a total of 146 amino acids. In particular, at position 6 the glutamic acid is replaced by valine. This example illustrates that in the study of diseases, methods for determining changes in the 3-dimensional structure of a protein are very valuable. Unfortunately, WO 00/08454 does not extend to include a study of the effects of subtle changes to the primary sequence of a protein molecule. Accordingly, the effect of a small number of differences in the primary sequence of a protein molecule, having for example more than 100 amino acid segments, on the CV spectrum of the protein molecule is currently not known.

SUMMARY OF THE INVENTION

In accordance with an aspect of the instant invention there is provided a method for distinguishing between protein variants, comprising the steps of: determining conditions for providing a plurality of different conformers for observation in a CV spectrum of a predetermined protein; using the determined conditions to selectively transmit ions including the different conformers of the predetermined protein through an analyzer region of a FAIMS; varying a CV that is applied to an electrode of the FAIMS so as to obtain a CV spectrum relating to the predetermined protein; obtaining, using the same determined conditions, a CV spectrum relating to an analyte protein; and, comparing features within the CV spectrum relating to the predetermined protein and features within in the CV spectrum relating to the analyte protein.

In accordance with another aspect of the instant invention there is provided a method for distinguishing between protein variants, comprising the steps of: providing a FAIMS analyzer region defined by a space between two spaced-apart electrodes; providing predetermined conditions within the FAIMS analyzer region; producing ions of an analyte protein from a solution having predetermined properties and including the analyte protein; introducing the ions of an analyte protein into the FAIMS analyzer region; detecting an intensity of the ions of an analyte protein that are transmitted through the FAIMS analyzer region at a predetermined CV value; determining a difference between the detected intensity and a reference value, the reference value relating to an expected intensity at the predetermined CV value for a reference form of the analyte protein; and, registering the analyte protein as a variant of the reference form in dependence upon the determined difference.

In accordance with another aspect of the instant invention there is described a use of high field asymmetric waveform ion mobility spectrometry for screening a solution sample containing a type of protein molecule, to identify one of a presence of and an absence of a variant of the protein molecule indicative of one of a diseased state and an abnormal state in an individual from which the sample is obtained.

In accordance with another aspect of the instant invention there is provided a method of detecting protein variants, comprising the steps of: providing a sample derived from a biological source to a FAIMS analyzer; sensing an ion output of the FAIMS analyzer; and, based upon the sensed ion output, identifying one of a presence of and an absence of a variant of the protein molecule indicative of one of a diseased state and an abnormal state in the biological source.

DESCRIPTION OF THE DRAWINGS

Exemplary embodiments of the invention will now be described in conjunction with the following drawings, in which similar reference numbers designate similar items:

FIG. 7($b$) shows a CV spectrum for the +17 charge state of the cow variant of cytochrome c;

FIG. 7($c$) shows a CV spectrum for the +17 charge state of the dog variant of cytochrome c;

FIG. 7($d$) shows a CV spectrum for the +17 charge state of the rat variant of cytochrome c;

FIG. 7($e$) shows a CV spectrum for the +17 charge state of the sheep variant of cytochrome c;

FIG. 8($b$) shows a CV spectrum for the +18 charge state of the cow variant of cytochrome c;

FIG. 8($c$) shows a CV spectrum for the +18 charge state of the dog variant of cytochrome c;

FIG. 8($d$) shows a CV spectrum for the +18 charge state of the rat variant of cytochrome c;

FIG. 8($e$) shows a CV spectrum for the +18 charge state of the sheep variant of cytochrome c;

FIG. 9($b$) shows the CV spectrum of FIG. 8($b$) with the baseline vertically expanded by a factor of 10;

FIG. 9($c$) shows the CV spectrum of FIG. 8($c$) with the baseline vertically expanded by a factor of 10;

FIG. 9($d$) shows the CV spectrum of FIG. 8($d$) with the baseline vertically expanded by a factor of 10; and, FIG. 9($e$) shows the CV spectrum of FIG. 8($e$) with the baseline vertically expanded by a factor of 10.

DETAILED DESCRIPTION OF THE DRAWINGS

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein. In the discussion that follows and in the claims, a predetermined protein is defined as a protein of interest having a given primary sequence of amino acids and is sometimes called a "reference" form of an analyte protein. An analyte protein is defined as a protein having a primary sequence that is at least similar to the primary sequence of the predetermined protein. If it is determined that the analyte protein has a primary sequence that is identical to that of the predetermined protein, then the analyte protein is referred to in this application as one of "normal", "a match", and "healthy". If it is determined that the analyte protein has a primary sequence that differs from that of the predetermined protein at a number of amino acid positions that is small relative to the total number of amino acid positions, then the analyte protein is called a variant of the predetermined protein, and is referred to in this application as one of "irregular", "a mismatch", and "diseased". If the predetermined protein comes from a healthy first individual of a type of organism, it is possible that a variant of the predetermined protein is associated with a diseased state. Of course, a diseased state may also arise when an analyte protein has a same sequence of amino acids as the predetermined protein. In this case, a three-dimensional structure of the analyte protein when in solution within the diseased organism differs from a structure that occurs within a healthy organism. In order for FAIMS to detect this type of diseased state, information relating to the structure of the analyte protein within the organism must be retained in the gas phase ion sample that is introduced into the FAIMS analyzer.

Figure 1:
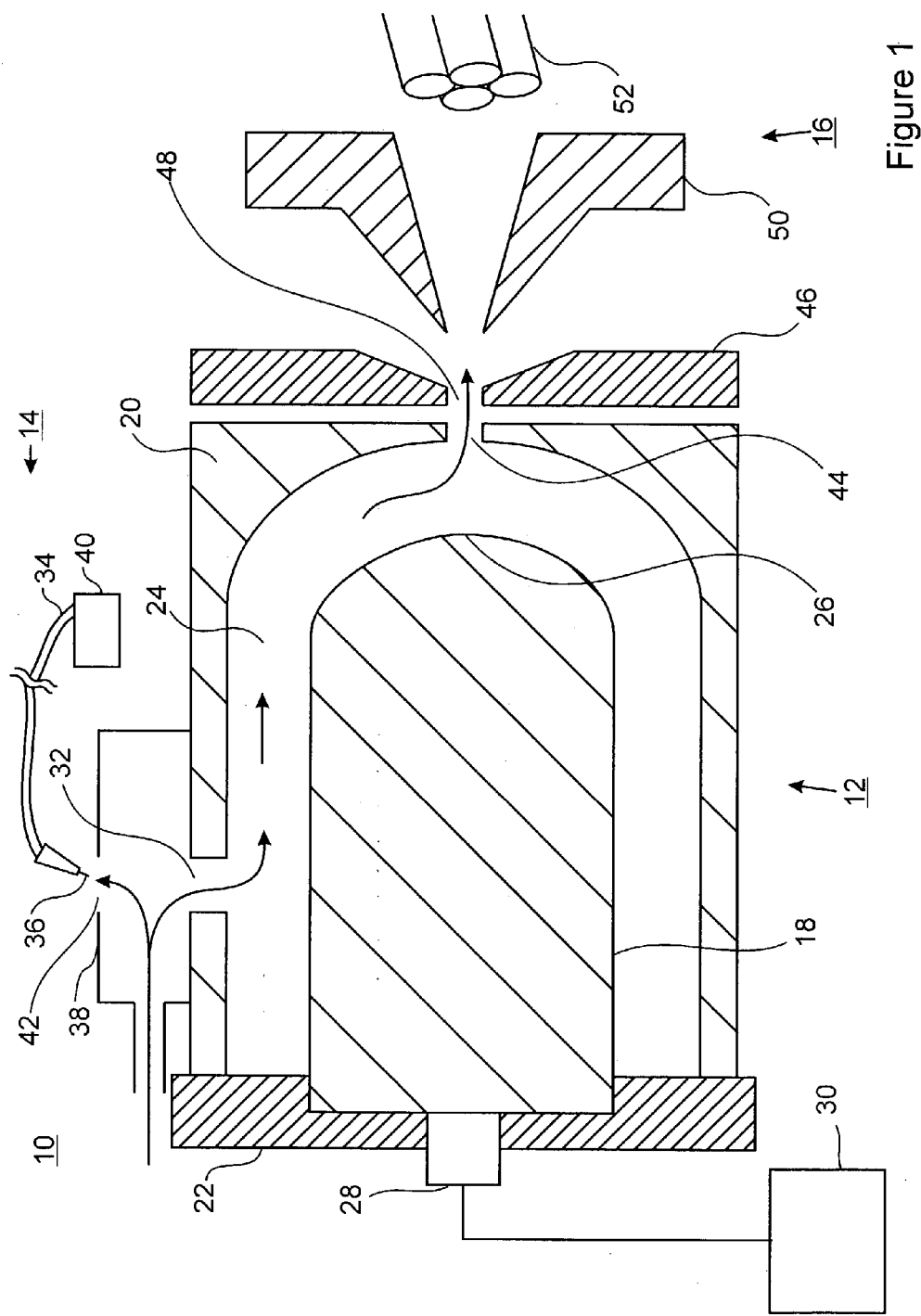
FIG. 1 is a simplified block diagram of a domed-FAIMS analyzer, an associated ionization source and an associated mass spectrometric detection system for use with a method according to the instant invention.

Referring to FIG. 1, shown is a non-limiting example of an apparatus that embodies a specific FAIMS electrode geometry, which is suitable for use with a method according to the instant invention. The apparatus, shown generally at 10, includes a FAIMS device 12 in the form of a domed-FAIMS analyzer, an associated ionization source 14 and an associated mass spectrometric detection system 16. However, it is to be clearly understood that, alternatively, any one of a plurality of other FAIMS electrode geometries is provided in place of the domed-FAIMS electrode geometry that is described with reference to FIG. 1. For instance, one of a parallel plate electrode geometry and a side-to-side geometry FAIMS optionally is provided as the FAIMS device 12. The domed-FAIMS analyzer 12 includes inner and outer cylindrical electrodes 18 and 20, respectively, supported by an electrically insulating material 22 in an overlapping, spaced-apart arrangement. The generally annular space between the inner electrode 18 and the outer electrode 20 defines a FAIMS analyzer region 24. The width of the analyzer region 24 is approximately uniform around the circumference of the inner electrode 18, and extends around a curved surface terminus 26 of the inner electrode 18. Inner electrode 18 is provided with an electrical contact 28 through the insulating material 22 for connection to a power supply 30 of the FAIMS 12, that during use is capable of applying a high voltage asymmetric waveform voltage (DV) and a low voltage dc compensation voltage (CV) to the inner FAIMS electrode 18. A particular type of ion is transmitted through the analyzer region 24 at a given combination of CV and DV, on the basis of the high field mobility properties of the ion.

An ion inlet orifice 32 is provided through the outer electrode 20 for introducing ions produced at the ionization source 14 into the analyzer region 24. For example, the ionization source 14 is in the form of an electrospray ionization ion source including a liquid delivery capillary 34, a fine-tipped electrospray needle 36 that is held at high voltage (power supply not shown) and a curtain plate 38 serving as a counter-electrode for electrospray needle 36. The liquid delivery capillary 34 is in fluid communication with sample reservoir 40 containing a solution of an ion precursor. Ions are produced by the very strong electric field at the electrospray needle 36 from the solution of an ion precursor. The potential gradient accelerates the ions away from the electrospray needle 36, towards the curtain plate electrode 38. A portion of the ions pass through an orifice 42 in the curtain plate electrode 38, become entrained in a flow of a carrier gas, which is represented in FIG. 1 by a series of closed-headed arrows, and are carried into the FAIMS analyzer region 24. The flow of a carrier gas is provided through the analyzer region 24 to carry the ions toward an ion outlet orifice 44 located opposite the curved surface terminus 26 of the inner electrode 18. The orifice 42 within the curtain plate electrode 38 allows for the flow of a portion of the carrier gas in a direction that is counter-current to the direction in which the ions are traveling near the ion inlet 32, so as to desolvate the ions before they are introduced into the analyzer region 24. Once inside the FAIMS analyzer region 24, the ions are transmitted through an electric field that is formed within the FAIMS analyzer region 24 by the application of the DV and the CV to the inner FAIMS electrode 18 via the electrical contact 28. Since the electric field also extends around the curved surface terminus 26, the transmitted ions tend to be directed generally radially inwardly towards the ion outlet orifice 44.

Referring still to FIG. 1, a mass spectrometer detector 16 is disposed external to the FAIMS analyzer region 24, and includes an orifice plate 46 having an inlet orifice 48 extending therethrough. As will be apparent to one of skill in the art, the size of the inlet orifice 48 is typically very small, being limited by the pumping efficiency of a not illustrated mass spectrometer vacuum system. The inlet orifice 48 in the orifice plate 46 is aligned with the ion outlet orifice 44 of the domed-FAIMS apparatus such that ions being extracted through the ion outlet orifice 44 enter the mass spectrometer inlet orifice 48. Those ions that pass through the orifice 48 in the orifice plate 46 travel to a skimmer cone 50 within the differentially pumped region of the mass spectrometer, and are analyzed within a mass analyzer 52 on the basis of their mass-to-charge ratio. The mass spectrometer includes a not illustrated detector, such as for instance an electron multiplier, for providing an electrical signal that is proportional to a detected indicator ion current.

Figure 2:
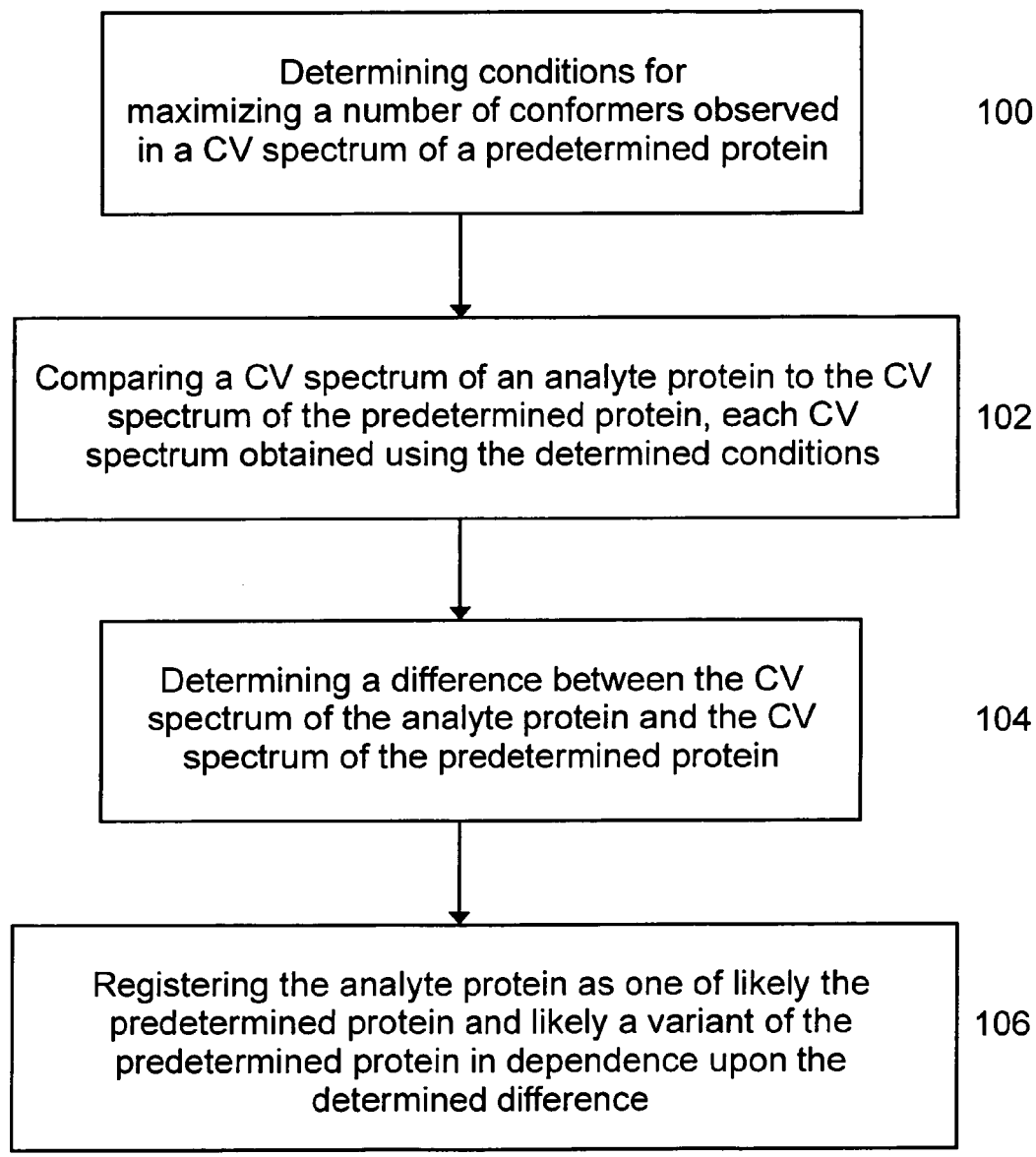
FIG. 2 shows a simplified flow diagram for a method of detecting a variant of a predetermined protein molecule according to the instant invention.

Referring now to FIG. 2, shown is a simplified flow diagram of a method for detecting a variant of a predetermined protein according to the instant invention. At step 100, conditions are determined for maximizing a number of conformers that are observed in a CV spectrum of the predetermined protein. For instance, at least one of the pH, temperature and composition of a solution containing the predetermined protein is adjusted. Optionally, conditions for transporting ions of the predetermined protein through the FAIMS, such as for instance one of the applied DV, the carrier gas composition and the temperature of the carrier gas, are adjusted. Step 100 may be performed in a trial and error fashion, for instance a CV spectrum is obtained following each incremental adjustment of one of the above-mentioned parameters, until an appropriate set of operating conditions is identified. At step 102, a CV spectrum of an analyte protein, which is obtained using the same conditions that were determined at step 100, is compared to the CV spectrum of the predetermined protein. At step 104, a difference is determined between the CV spectrum of the analyte protein and the CV spectrum of the predetermined protein. Some non-limiting examples of the difference that is determined include i) a difference in the CV location of a peak maximum in the CV spectrum of the analyte protein compared to the CV location of a peak maximum in the CV spectrum of the predetermined protein, ii) a difference in the relative intensities of two peaks in the CV spectrum of the analyte protein compared to the relative intensities of two peaks at the same CV locations in the CV spectrum of the predetermined protein, and iii) a difference in the intensity of a peak at a CV location in the CV spectrum of the analyte protein relative to the intensity of a peak at the same CV location in the CV spectrum of the predetermined protein. At step 106, the analyte protein is registered as a variant of the predetermined protein in dependence upon the determined difference. Of course, absent a determined difference between the CV spectra, such as for instance when the CV spectrum of the predetermined protein and the CV spectrum of the analyte protein are substantially similar, the analyte protein is registered as normal.

Figure 3:
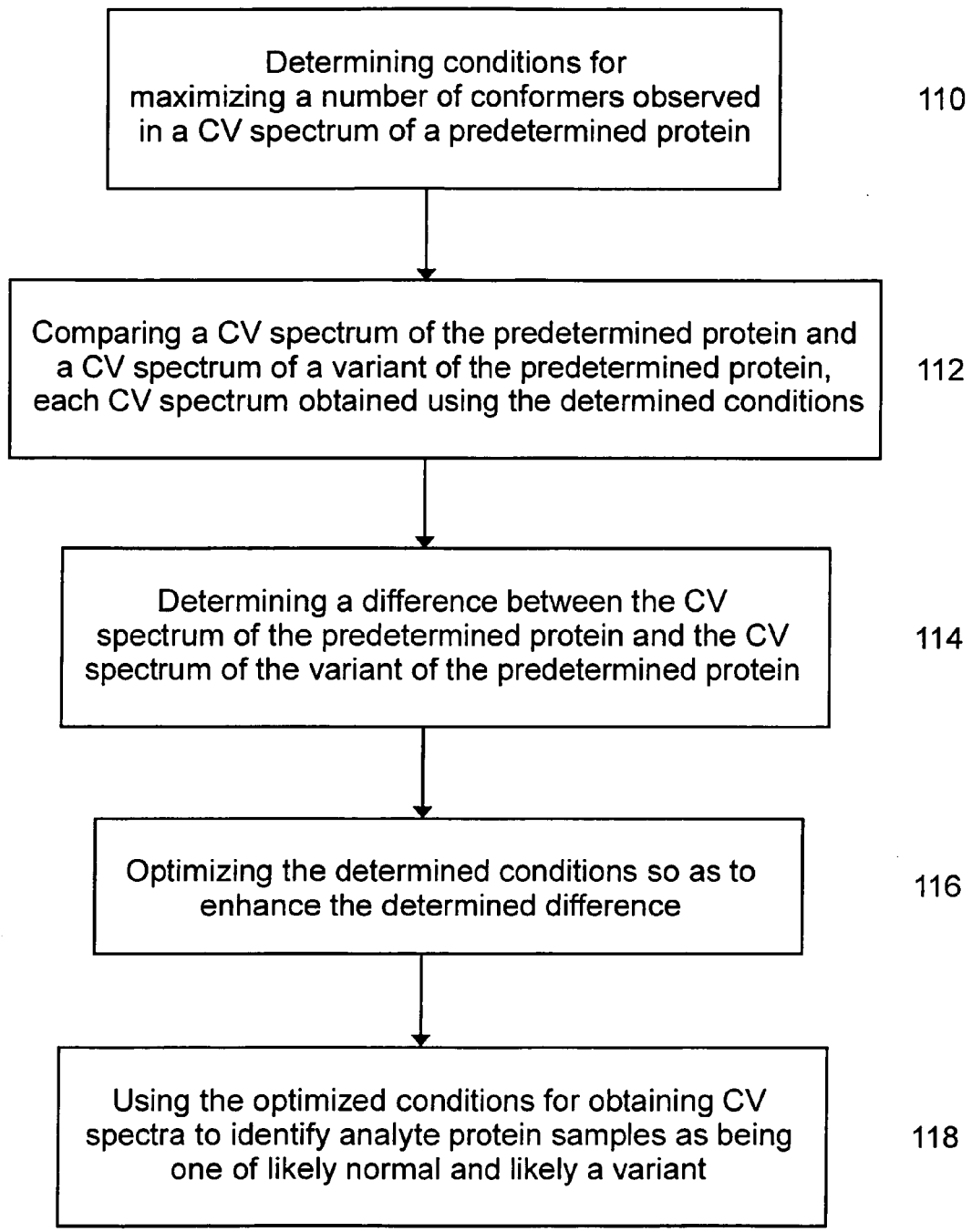
FIG. 3 shows a simplified flow diagram for another method of detecting a variant of a predetermined protein molecule according to the instant invention.

Referring now to FIG. 3, shown is a simplified flow diagram of another method for detecting a variant of a predetermined protein molecule according to the instant invention. At step 110, conditions are determined for maximizing a number of conformers observed in a CV spectrum of the predetermined protein. For instance, at least one of the pH, temperature and composition of a solution containing the predetermined protein is adjusted. Optionally, conditions for transporting ions of the predetermined protein through the FAIMS, such as for instance one of the applied DV, the composition of a carrier gas, and a temperature of the carrier gas, are adjusted. Step 110 may be performed in a trial and error fashion, for instance a CV spectrum is obtained following each incremental adjustment of one of the above-mentioned parameters, until an appropriate set of operating conditions is identified. At step 112, a CV spectrum of a variant of the predetermined protein, which is obtained using the same conditions that were determined at step 110, is compared to the CV spectrum of the predetermined protein. At step 114, a difference is determined between the CV spectrum of the predetermined protein and the CV spectrum of the variant of the predetermined protein. Some non-limiting examples of the difference that is determined include i) a difference in the CV location of a peak maximum in the CV spectrum of the variant of the predetermined protein compared to the CV location of a peak maximum in the CV spectrum of the predetermined protein, ii) a difference in the relative intensities of two peaks in the CV spectrum of the predetermined protein compared to the relative intensities of two peaks at the same CV locations in the CV spectrum of the variant of the predetermined protein, and iii) a difference in the intensity of a peak at a CV location in the CV spectrum of the predetermined protein relative to the intensity of a peak at the same CV location in the CV spectrum of the variant of the predetermined protein. At step 116, the conditions determined at step 110 are further optimized, such that the determined difference between the CV spectrum of the predetermined protein and the CV spectrum of the variant of the predetermined protein is enhanced. In this method, the variant is used to establish operating conditions that enhance the likelihood of observing differences between the CV spectra of a predetermined protein and its variants. At step 118, the optimized conditions of step 116 are used to obtain CV spectra relating to other samples. The CV spectra relating to other samples are then, for example, compared to CV spectra of the predetermined protein, which were also obtained using the optimized conditions. When a CV spectrum relating to one of the other samples is substantially similar to the CV spectrum of the predetermined protein, then a protein contained in the other sample is identified as being likely normal. Of course, when a CV spectrum relating to one of the other samples differs from the CV spectrum of the predetermined protein, then a protein contained in the other sample is identified as being likely a variant. In this way, a plurality of unknown samples may be screened rapidly using FAIMS, to determine the presence of likely variant forms of a predetermined protein that may, for instance, be indicative of a diseased state in an organism from which the unknown sample was obtained.

Figure 4:
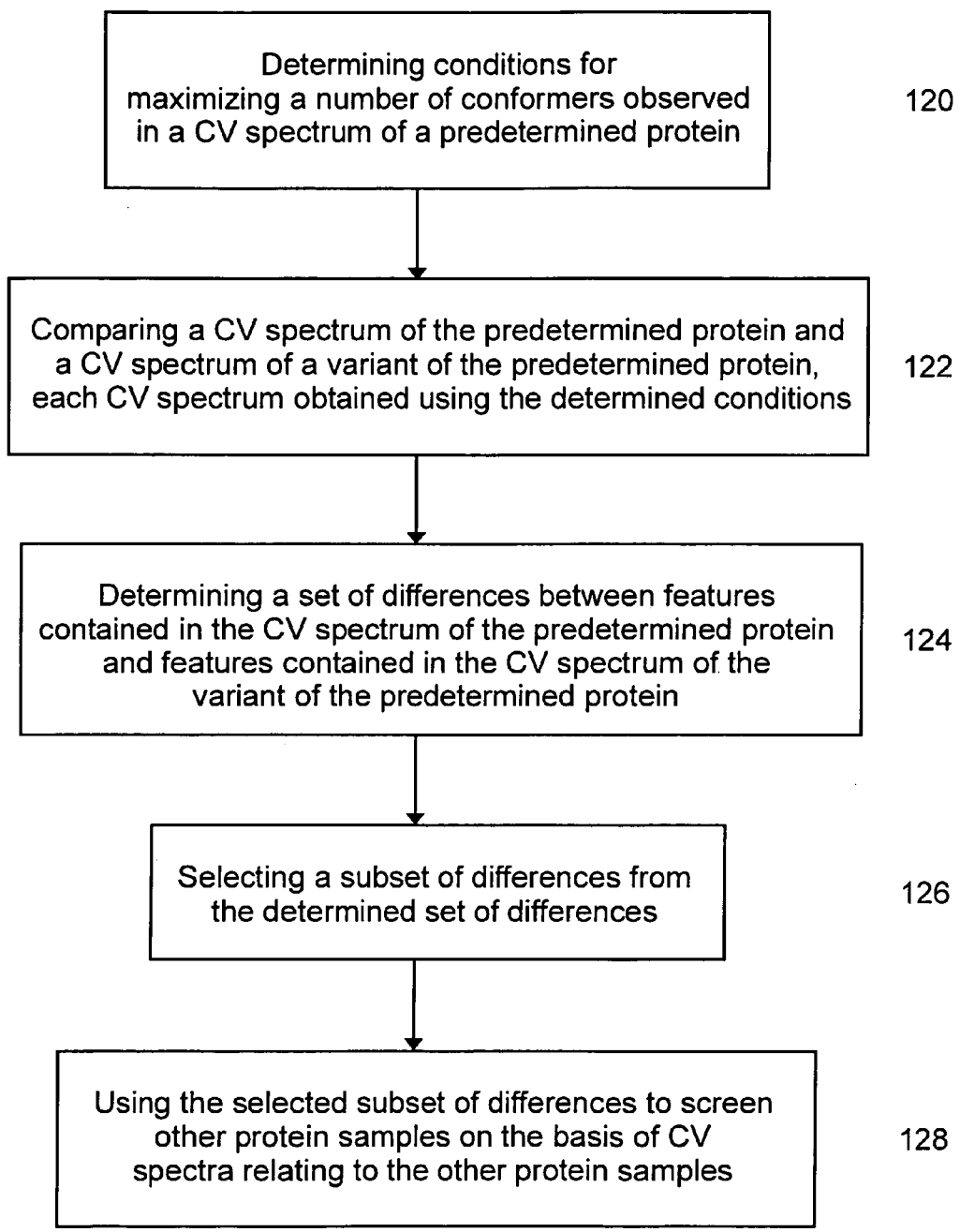
FIG. 4 shows a simplified flow diagram for another method of detecting a variant of a predetermined protein molecule according to the instant invention.

Referring now to FIG. 4, shown is a simplified flow diagram of another method for detecting a variant of a predetermined protein molecule according to the instant invention. At step 120, conditions are determined for maximizing a number of conformers observed in a CV spectrum of a predetermined protein. For instance, at least one of the pH, temperature and composition of a solution containing the predetermined protein molecule is adjusted. Optionally, conditions for transporting ions of the predetermined protein through the FAIMS, such as for instance one of the applied DV, the carrier gas composition, and a temperature of the carrier gas, are adjusted. Step 120 may be performed in a trial and error fashion, for instance a CV spectrum is obtained following each incremental adjustment of one of the above-mentioned parameters, until a suitable CV spectrum of the predetermined protein is obtained. At step 122, a CV spectrum of the predetermined protein is compared to a CV spectrum of a variant of the predetermined protein, both CV spectra being obtained using the conditions that were determined at step 120. At step 124, a set of differences between features contained in the CV spectrum of the predetermined protein and features contained in the CV spectrum of the variant of the predetermined protein are determined. Some non-limiting examples of the differences between features that may be determined include i) a difference in the CV location of a peak maximum in the CV spectrum of the predetermined protein compared to the CV location of a peak maximum in the CV spectrum of the variant of the predetermined protein, ii) a difference in the relative intensities of two peaks in a the CV spectrum of the predetermined protein compared to the relative intensities of two peaks at the same CV locations in the CV spectrum of the variant of the predetermined protein, and iii) a difference in the intensity of a peak at a CV location in the CV spectrum of the predetermined protein relative to the intensity of a peak at the same CV location in the CV spectrum of the predetermined protein. At step 126, a subset of the determined set of differences is determined. For instance, the subset includes differences for which a predetermined threshold value can be defined, so as to maximize a probability that differences between CV spectra will lead to the correct identification. As an example, a difference in the CV locations of peak maxima is included in the subset of differences only when the intensity in the CV spectrum of a variant sample at the CV location of a peak maximum in a CV spectrum of the predetermined protein is less than approximately 10% of the intensity at the same CV value in a CV spectrum of the predetermined protein. The subset of differences provides a means for detecting the presence of a variant of the predetermined protein in other samples. For instance, a plurality of unknown samples containing protein molecules may be screened rapidly using FAIMS. The CV spectrum, or alternatively data collected at selected CV values, of an unknown sample is compared to the CV spectrum of the predetermined protein to determine differences therebetween. If the differences correlate with the subset of differences, then the unknown sample is identified as likely containing the variant of the predetermined protein. Of course if the differences do not correlate with the subset of differences, such as for instance when the CV spectrum of the predetermined protein and the CV spectrum of the unknown sample are substantially similar, then the unknown sample is identified as likely containing the normal form of the predetermined protein.

Figure 5:
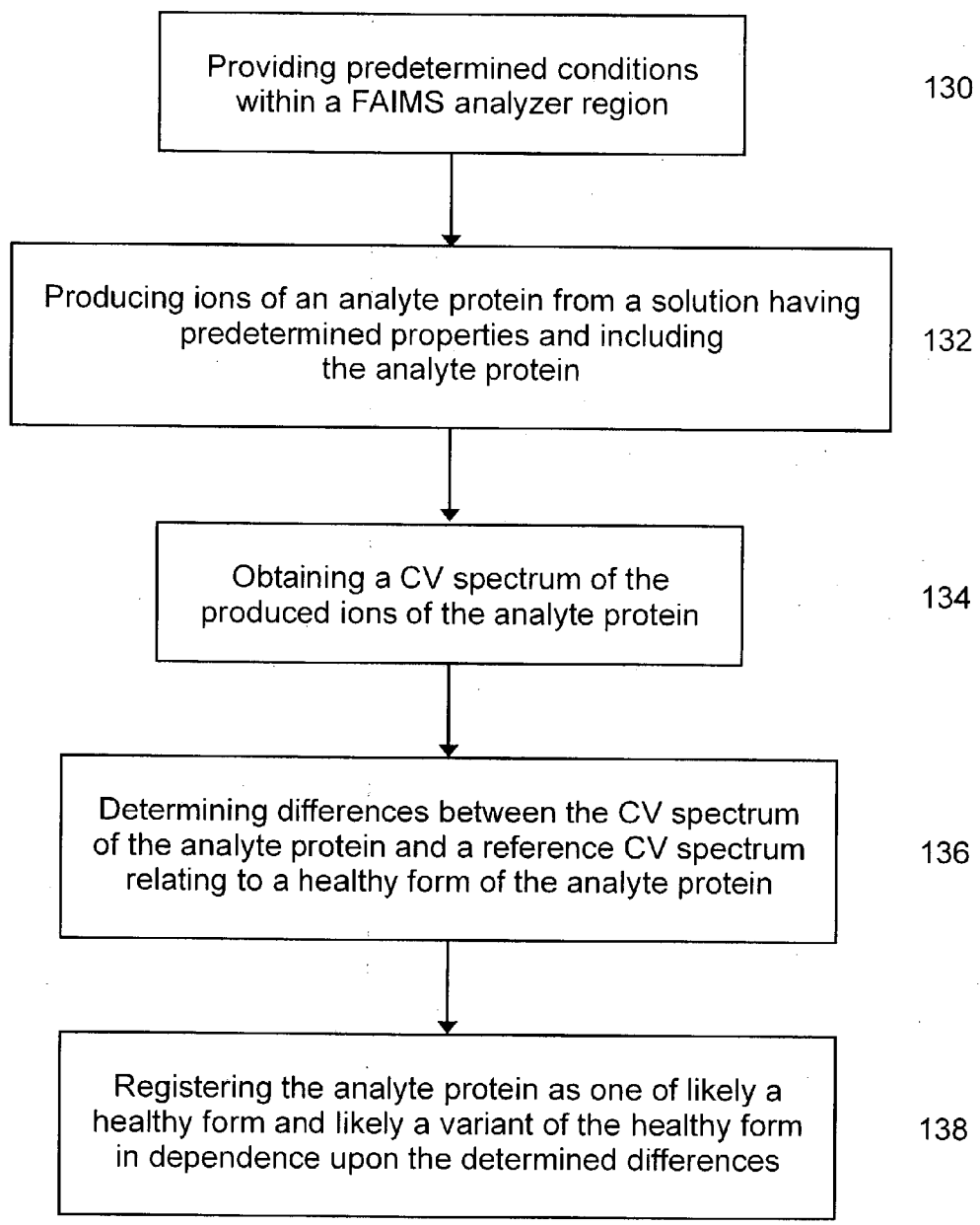
FIG. 5 shows a simplified flow diagram for another method of detecting a variant of a predetermined protein molecule according to the instant invention.

Referring now to FIG. 5, shown is a simplified flow diagram for another method of detecting a variant of a predetermined protein molecule according to the instant invention. In particular, the method of FIG. 5 is for use with a FAIMS apparatus to rapidly screen a sample to determine whether or not the sample contains the variant of the predetermined protein molecule. At step 130, predetermined conditions are provided within an analyzer region of the FAIMS apparatus. At step 132, ions of an analyte protein are produced from a solution having predetermined properties and containing the analyte protein. Preferably, the predetermined conditions that are provided within the analyzer region of the FAIMS and the predetermined properties of the solution are determined in advance, and this determination is not a part of the method of FIG. 5. For instance, a standardized method is determined in advance for analyzing the predetermined protein molecule. The standardized method defines operating parameters for obtaining the CV spectrum of the predetermined protein. The operating parameters are identical to operating parameters used to obtain a reference CV spectrum, or at least a part thereof, relating to a "healthy" form of the predetermined protein molecule. Preferably, a library of such standardized methods is available, the library including a plurality of different standardized methods, one each for analyzing a different predetermined protein. Optionally, the predetermined conditions within the analyzer region of the FAIMS are pre-set, for analyzing only a single predetermined protein, or for analyzing a small number of different predetermined proteins under identical conditions. At step 134, the produced ions of the analyte protein are introduced into the FAIMS analyzer region and a CV spectrum of the produced ions is obtained. At step 136, differences are determined between the CV spectrum of the analyte protein and the reference CV spectrum relating to the "healthy" form of the predetermined protein. At step 138, the analyte protein is registered as one of likely a healthy form and likely a variant of the healthy form of the predetermined protein, in dependence upon the determined difference. Of course, absent a determined difference between the CV spectra, such as for instance when the reference CV spectrum and the CV spectrum of the analyte protein are substantially similar, the analyte protein is registered as normal.

Figure 6:
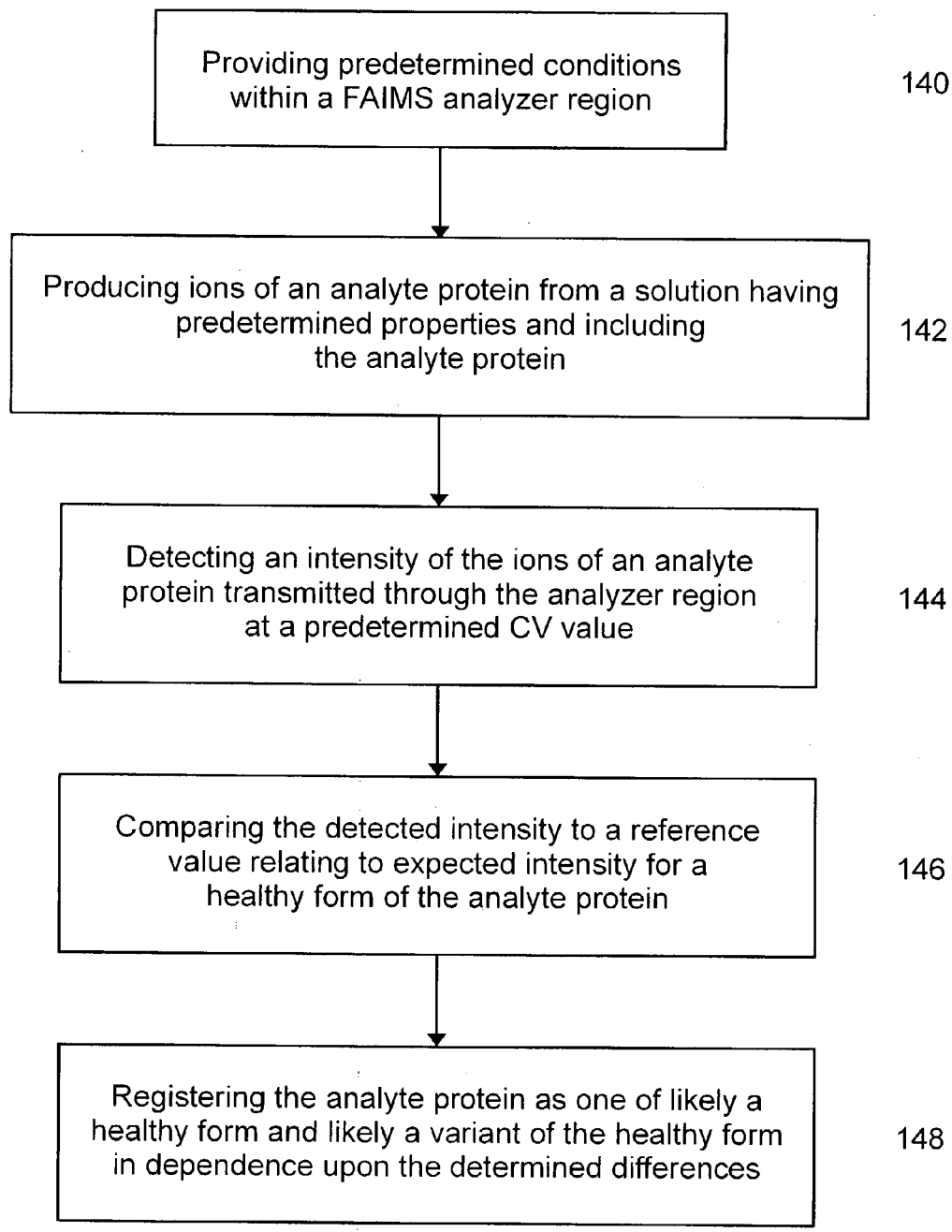
FIG. 6 shows a simplified flow diagram for another method of detecting a variant of a predetermined protein molecule according to the instant invention.
Figure 7:
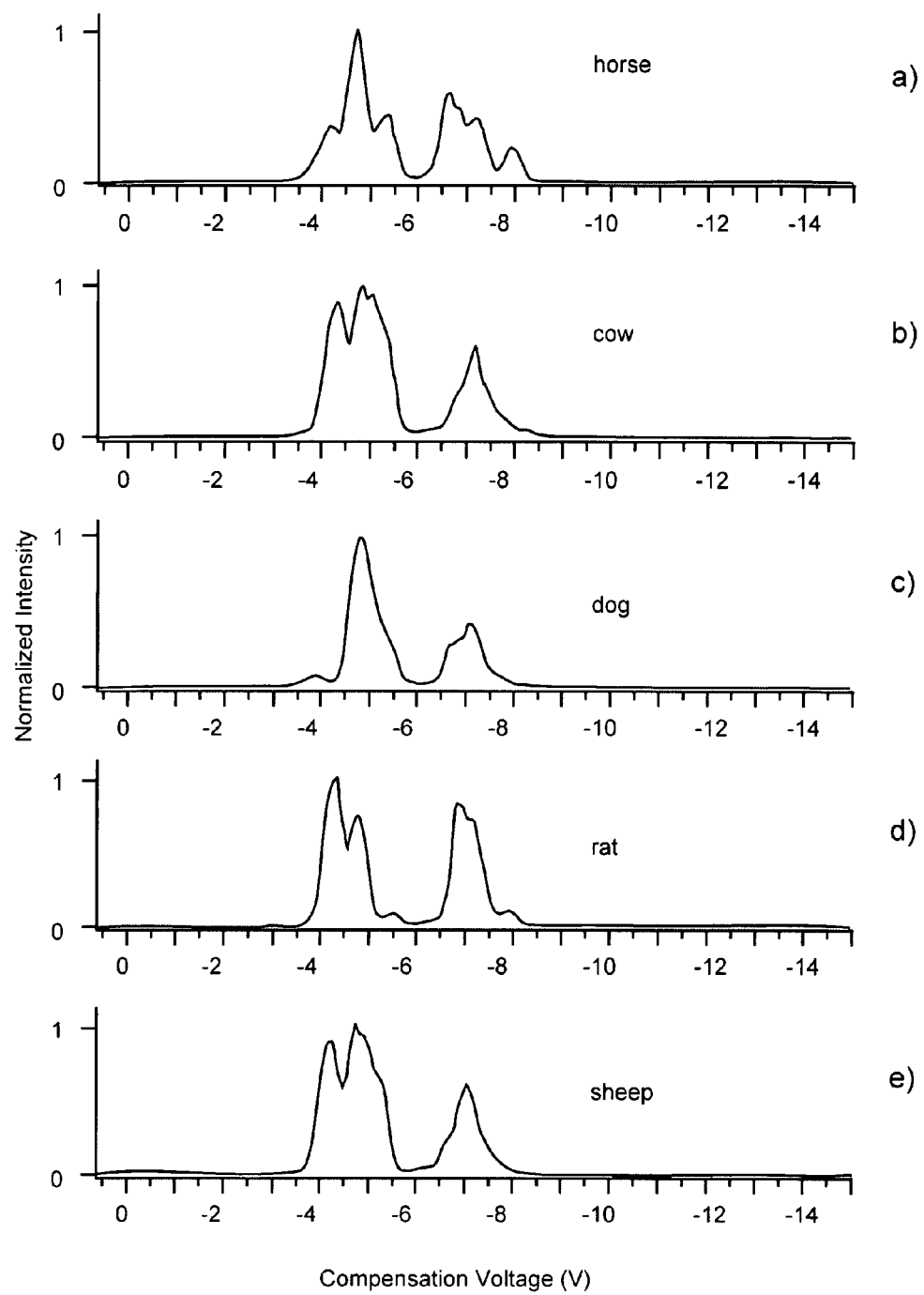
FIG. 7($a$) shows a CV spectrum for the +17 charge state of the horse variant of cytochrome c.
Figure 8:
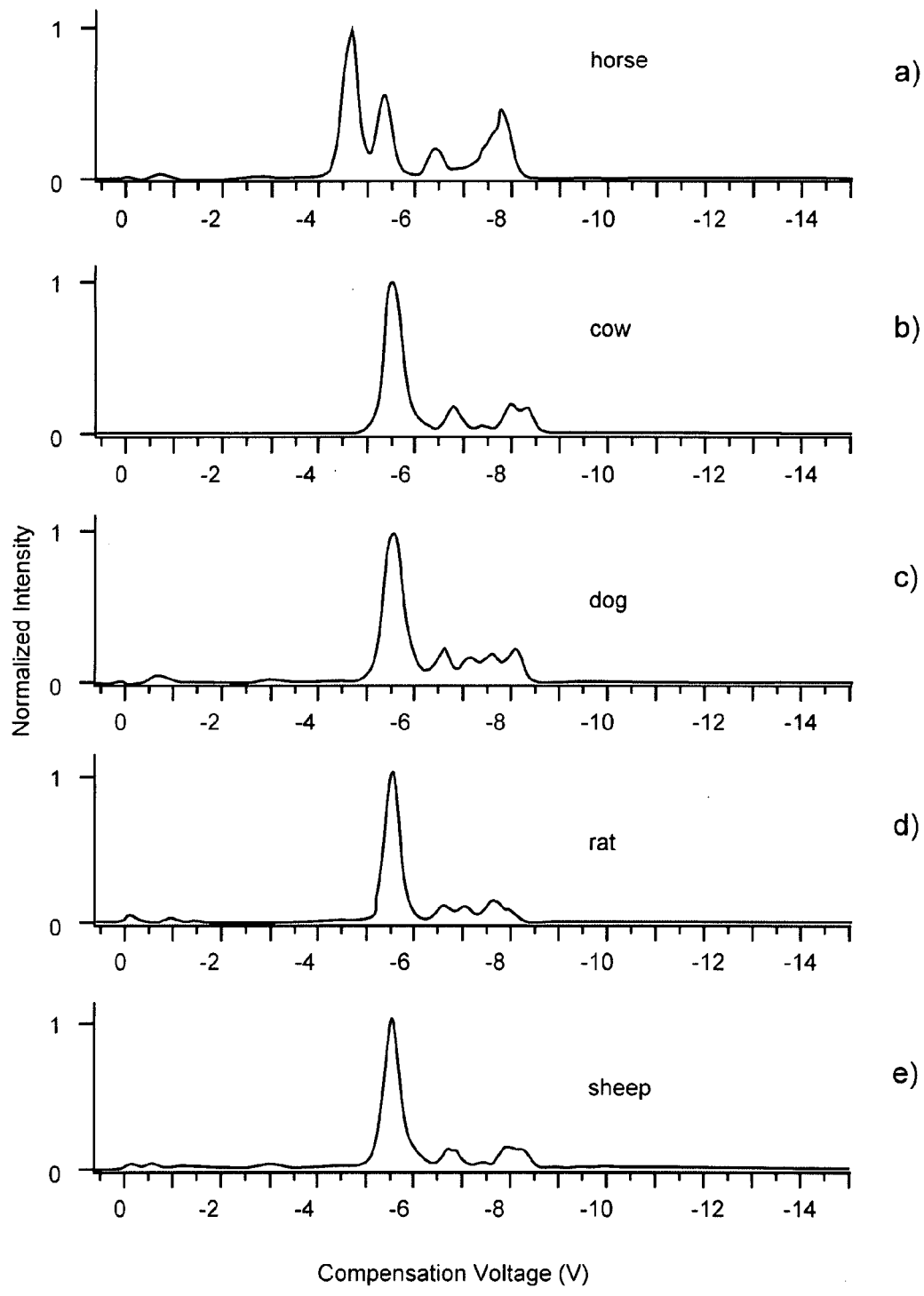
FIG. 8($a$) shows a CV spectrum for the +18 charge state of the horse variant of cytochrome c.

FIG. 6 shows a simplified flow diagram for another method of detecting a variant of a predetermined protein molecule according to the instant invention. In particular, the method of FIG. 6 is for use with a FAIMS apparatus to rapidly screen a sample to determine whether or not the sample contains a variant of the predetermined protein. At step 140, predetermined conditions are provided within an analyzer region of the FAIMS apparatus. At step 142, ions of an analyte protein are produced from a solution having predetermined properties and containing the analyte protein. Preferably, the predetermined conditions that are provided within the analyzer region of the FAIMS and the predetermined properties of the solution are determined in advance, and this determination is not a part of the method of FIG. 6. For instance, a standardized method is determined in advance for analyzing the predetermined protein. The standardized method defines operating parameters for obtaining the CV spectrum of the predetermined protein. The operating parameters are identical to operating parameters used to obtain a reference CV spectrum, or at least a part thereof, relating to a "healthy" form of the predetermined protein. Preferably, a library of such standardized methods is available, the library including a plurality of different standardized methods, one each for analyzing a different predetermined protein. Optionally, the predetermined conditions within an analyzer region of the FAIMS are pre-set, for analyzing a single predetermined protein, or for analyzing a small number of predetermined proteins under identical conditions. At step 144, the CV applied to the FAIMS is set to a predetermined value and an intensity of the ions of the analyte protein being transmitted through the FAIMS is detected. Optionally, step 144 is repeated at a different CV value. At step 146, the detected intensity is compared to a reference value relating to an expected intensity for the "healthy" form of the predetermined protein. At step 148, the analyte protein is registered as one of likely a healthy form and likely a variant of the healthy form of the predetermined protein, in dependence upon the determined difference. Of course, absent a determined difference, such as for instance when the reference expected intensity and the intensity of the analyte protein at a predetermined CV value are substantially similar, the analyte protein is registered as normal.

Particular features of the instant invention will now be illustrated, with reference to the following specific and non-limiting example. In the instant example, several different variants of the protein cytochrome c are studied, including; a horse variant, a rat variant, a sheep variant, a cow variant and a dog variant. The information generated from the CV spectra of these five variants of cytochrome c, analyzed as solutions of 50:50:1 water/methanol/acetic acid (v/v/v), is sufficient to be able to discriminate between the different protein variants. Of course, the variants of cytochrome c in this example are not indicative of any particular diseased state. The instant example is provided in order to demonstrate that the CV spectra obtained using FAIMS, in accordance with the above methods, contain sufficient information for discriminating between variants of a protein.

Each one of the five above-mentioned variants of cytochrome c contains 104 amino acids. The cow and sheep variants have the same primary sequence of amino acids, whereas the other three variants each differ from cow/sheep by the replacement of three amino acids; that is, three amino acids are replaced with another amino acid. The horse variant differs at amino acid 47 (S-T), 60 (G-K), and 89 (G-T); the rat variant differs at amino acid 44 (P-A), 62 (E-D), and 92 (E-A); and the dog variant differs at amino acid 88 (K-T), 92 (E-A), and 103 (N-K) where the letters D, A etc. are common short forms for the various amino acids. For instance, A is a common short form for the amino acid alanine and D is a short form for the amino acid aspartic acid, etc.

The horse, rat, sheep, cow, and dog cytochrome c variants were obtained in powdered form. Stock solutions of each of the five variants of cytochrome c were prepared separately by dissolving a known amount of each variant in a volume of distilled/deionized water (DDW). Running solutions were prepared by combining known amounts of the stock solution, DDW, HPLC grade methanol (methanol), and ACS grade glacial acetic acid (acetic acid) so that the concentration of the variant was approximately 2 µM and the solvent was a mixture of approximately 49.5% DDW, 49.5% methanol, and 1% acetic acid (v/v/v). For example, to prepare 2 mL of a running solution, the following solutions were transferred to a glass vial using eppendorf pipets: 990 µL of methanol, 980 µL of DDW, 10 µL of a 400 µM stock solution, and 20 µL of acetic acid. The glass vial was sealed with a screw top cap and shaken to ensure homogeneity of the solution.

An apparatus similar to the one that is shown generally at 10 in FIG. 1 was used to acquire the CV spectra for the five variants of cytochrome c. Specifically, the apparatus includes a domed-FAIMS analyzer 12, an electrospray ionization source 14 and a mass spectrometer detector 16 in the form of an API 300 triple quadrupole mass spectrometer. For this series of experiments, an electrospray ionization needle was prepared using a new piece of fused silica capillary of approximately 50 cm in length and having a 50 µm inner diameter and a 180 µm outer diameter. The piece of fused silica was fitted into a 10-cm long stainless steel capillary having a 200 µm inner diameter and a 430 µm outer diameter, and allowed to protrude about 1 mm beyond the end of the stainless steel. This stainless steel capillary, in turn, protruded about 5 mm beyond the end of a larger stainless steel capillary of approximately 15 cm in length and having a 500 µm inner diameter and a 1.6 mm outer diameter, which was used for structural support and application of the high voltage necessary for electrospray. A Harvard® Apparatus Model 22 syringe pump was used to deliver the solution from a 250 µL syringe to the end of the fused silica capillary at a flow rate of 1 µL/min.

The 250 µL syringe was rinsed at least 3 times with a solution blank, such as for example a solution without the cytochrome c variant present, and including approximately 49.5% DDW, 49.5% methanol, and 1% acetic acid (v/v/v). The 250 µL syringe was rinsed a minimum of three times with a protein variant running solution before filling the 250 µL syringe with the protein variant running solution. The 250 µL syringe was hooked up to an associated liquid delivery system that was used to transfer the running solution from the 250 µL syringe to an electrospray ionization needle. Of course, between the analysis of running solutions having different dissolved protein variants, a syringe containing the solution blank was attached to the associated liquid delivery system for a period of time to flush through the running solution of a previous variant at a flow rate of 1 µL/min, prior to the analysis of a next running solution. When the relative intensity of the most intense peak in the CV spectrum of each charge state of the previous variant was less than 1% of its value in the running solution of the previous variant, the delivery system was deemed to be clean for the purpose of running the next sample solution. If the intensity did not drop to less than 1% after 5 minutes, the solution blank was replaced by a fresh solution blank, and the relative intensities of the most intense peak in the CV spectrum of each charge state of the previous variant were again monitored until the intensity dropped to less than 1% of its value in the running solution.

The tip of the electrospray needle 36 was placed approximately 1 cm away from, and slightly off-centre at an angle of approximately 45 degrees to, the curtain plate electrode 38 of the domed-FAIMS device of FIG. 1. Such an orientation of the electrospray needle 36 avoids the transfer of large droplets into the FAIMS analyzer region 24. The electrospray needle 36 was held at approximately 4100 V generating a current of about 180 nA while electrospraying each of the running solutions of the five variants. To optimize the electrospray process, the distance that the fused silica capillary protruded from the 10 cm long stainless steel capillary was adjusted until the current was stable at a value near 180 nA. The voltage on the curtain plate electrode 38 was 1000 V and the curtain plate electrode 38 was isolated from the outer electrode 20. The outer electrode 20 made electrical contact with the orifice plate 46 of the mass spectrometer 16, which were both held at +10 V. The domed-FAIMS 12 was operated in P2 mode; that is to say the asymmetric waveform has a negative DV value. The width of the FAIMS analyzer region 24 was approximately 2 mm, and the width of an extraction region intermediate the curved surface terminus 26 of the inner electrode 18 and the ion outlet orifice 44 was approximately 2.2 mm.

To generate the asymmetric waveform for the analyses described herein, a tuned electronic circuit was used that provided an appropriate combination of a sinusoidal wave and its harmonic to the inner electrode 18. These waveforms are mathematically described by the equation, $$V_a(t) = C + fD\sin(\omega t) + (1-f)D\sin(2\omega t - \phi) \quad (1)$$

where $V_a(t)$ represents the voltage of the waveform relative to the voltage applied to the outer electrode 20 at a given time, t, C is the compensation voltage, CV, which is changed stepwise from 1.12 to −15.28 V during the acquisition of the spectra as is described below, D is the maximum voltage of the waveform or the dispersion voltage, DV=−4400 V, $f$ is approximately 0.65, $\omega$ is the frequency (750 kHz), and $\phi$ is 90°.

Industrial grade nitrogen gas was passed through a charcoal/molecular sieve filter and introduced into the curtain gas inlet of FAIMS at a flow rate of 2 L/min. As is shown in FIG. 1, the total gas flow splits into two portions including a first portion flowing out through the curtain plate orifice 42 in a direction that is countercurrent to the arriving electrospray ions, thereby facilitating desolvation of the electrospray ions. A second portion of the total gas flow carries the ions inward through the ion inlet orifice 32 in the outer FAIMS electrode 20 and along the analyzer region 24 of the device. Ions transmitted by the FAIMS device were detected using an API 300 triple quadrupole mass spectrometer.

Electrospray ionization of cytochrome c produces a distribution of ions of the form $[M+zH]^{z+}$, where M is the MW of the variant, z is a number (e.g., 7,8,9), and H is a proton. The value of z in this example refers to the electrostatic charge state of the ion, for instance z=7 if the ion has a net electric charge of +7 originating from addition of 7 protons to the neutral protein molecule. For analyzing electrospray generated ions of the different variants of cytochrome c, the m/z values of several charge states were monitored as the CV was scanned, while electrospraying the running solution of each variant. Using the same solution and operating conditions, this measurement was repeated for different charge states until all the desired charge states were analyzed.

For example, when analyzing the running solution containing the horse variant of cytochrome c, the CV was scanned from 1.12 to −15.28 V in 170 incremental steps of approximately −0.096 V each. In one CV scan, charge states (z) 5 through 12 were monitored. This means that the following m/z values were monitored: 2473.0 (z=5), 2061.0 (z=6), 1766.7 (z=7), 1546.0 (z=8), 1374.3 (z=9), 1237.0 (z=10), 1124.6 (z=11), and 1031.0 (z=12). When the CV scan was initiated, the CV value was 1.12 V and the quadrupole mass analyzer began to selectively detect, one at a time, each of the eight m/z values listed above for a period of 300 ms each. After the ion intensities at all 8 m/z values were measured, the CV was stepped to 1.024 V and each of the eight m/z values were selectively detected, one at a time, again. This process of stepping the CV and selectively detecting the eight m/z values was repeated until a total of 171 points for each m/z value were obtained. From this data, a plot of the ion intensity as a function of the CV could be made for each charge state. In a second CV scan, using an identical range and step size, charge states 13 through 20 were monitored in an analogous way as described for charge states 5 through 12 with the exception that the m/z values were changed to 951.8 (z=13), 883.9 (z=14), 825.0 (z=15), 773.5 (z=16), 728.1 (z=17), 687.7 (z=18), 651.5 (z=19), and 619.0 (z=20).

The remaining variants of cytochrome c were analyzed separately in an analogous way, except that the m/z values of the +5 to +20 charge states were adjusted during the analysis of the running solution of the different variants based on the molecular weight of each particular variant. The molecular weights of the variants that were used in calculating the m/z ratios were 12 360 (horse), 12 230 (cow and sheep), 12 132 (rat), and 12 159 (dog).

The variants were analyzed in the order of horse, cow, dog, rat, and then sheep. After one variant was analyzed, the 250 μL syringe was rinsed in the procedure described above and the associated liquid delivery system was flushed in the manner described earlier.

FIGS. 7(a) to 7(e) show CV spectra that were obtained for the +17 charge state of the horse, cow, dog, rat, and sheep variants of cytochrome c. The m/z values that were monitored to obtain these spectra were 728.1 (horse), 720.4 (cow and sheep), 716.2 (dog), and 714.6 (rat). The x-axis shows the compensation voltage from 0.5 to −15 V. The data that is presented in FIGS. 7(a) to 7(e) has been normalized in order to facilitate comparisons between the five spectra. Since the cow and sheep variants have the same primary amino acid sequence, a comparison of the CV scans for the cow and sheep variants can be used to illustrate the reproducibility when comparing CV based fingerprint type spectra of two proteins. Since the primary amino acid sequence of the cow and sheep variants of cytochrome c were identical, it was expected that the CV spectra of the +17 ion of these two kinds of cytochrome c would be identical. FIGS. 7(b) to 7(e) show that the CV traces are very similar for cow and sheep, and illustrate the similarity that would be expected for measurements of identical proteins. Unlike the CV spectra of the cow/sheep variants, which were very similar, the three other variants all show some significant differences in their CV spectra for this charge state and set of solution conditions. The changes in the CV spectra include differences in relative CV values, peak intensities, and number of peaks. For example, all four CV spectra of cytochrome c variants from horse, cow, dog and rat show differences one to the other that are more easily observed than the differences between the cow and sheep variants of cytochrome c. The pattern of peaks and their relative intensities in the CV spectrum is considered to comprise a "fingerprint" for the protein.

FIGS. 8(a) to 8(e) show the CV spectra that were obtained for the +18 charge state of the horse, cow, dog, rat, and sheep variants of cytochrome c. The m/z values that were monitored to obtain these spectra were 687.7 (horse), 680.4 (cow and sheep), 676.5 (dog), and 675.0 (rat). The same CV scale is used that was used in FIG. 7 and again the y-axis, which represents the intensity, has been normalized. FIGS. 9(a) to 9(e) shows the same CV spectra as FIGS. 8(a) to 8(e), except that there has been an expansion of the vertical intensity scale of FIGS. 9(a) to 9(e) by a factor of 10. The CV spectra of the cow and sheep variants each show peak maxima at ten CV values, approximately at −0.1, −0.5, −1.3, −2.9, −4.3, −5.5, −6.8, −7.4, −7.9, and −8.3 V. Despite the abundance of information in the CV spectra of the cow and sheep variants, the spectra are almost identical with only slight differences in the intensities of the various-peaks that are partially attributable to the step size of CV used in acquiring the data. For example, the peaks in FIGS. 9(b) and 9(e) at a CV of approximately −0.1 V are very narrow, and the approximately 0.096 V step sizes that were used have resulted in a slightly distorted peak shape since the number of points that define the peak are insufficient for proper sampling. Smaller step sizes, such as for example a step size of 0.04 V, would allow for more points to be sampled, which would result in a better representation of the true peak shape.

Figure 9:
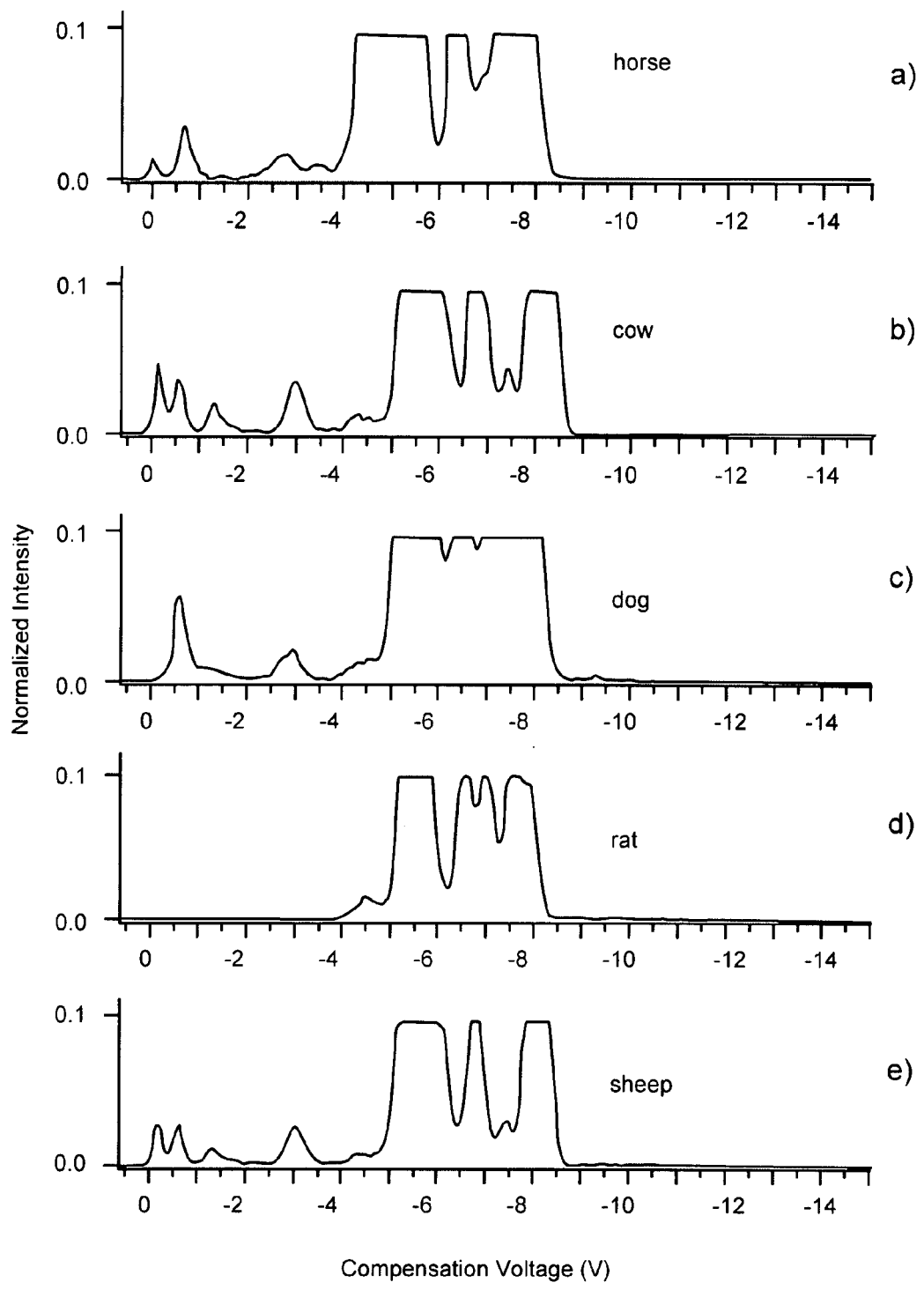
FIG. 9($a$) shows the CV spectrum of FIG. 8($a$) with the baseline vertically expanded by a factor of 10.

Although there some are similarities between the CV spectra obtained for each of the five variants of cytochrome c, there are also several differences. In addition to differences in relative intensities of the individual peaks, there are diagnostic changes that are observed among the five variants. For example, the horse variant shows a very large peak at a CV value of −4.7 V in FIG. 8(a). The other variants show little or no signal intensity at this CV value, indicating that the horse variant has a different preferred gas-phase conformation for this charge state compared with the other variants. In addition, other diagnostic examples include the dog variant being the only one that does not show a peak in its CV spectrum at approximately −0.1 V, as shown in FIG. 9(c), and the rat variant not showing a peak in its CV spectrum near −3 V, as shown in FIG. 9(d). The absence of these peaks in their respective CV spectra indicate that these variants cannot adopt these gas-phase conformations transmitted at these respective CV values because of the alteration in their primary sequence.

The above example demonstrates that the separation of gas-phase protein conformers using FAIMS, followed by mass spectral analysis, permits a detailed investigation of proteins, at all levels from primary amino acid sequence through to protein folding. This sensitive multi-dimensional "fingerprint" measurement permits the identification of subtle differences in proteins that have very similar structures, and therefore permits identification of proteins that are involved in diseases. The appearance of the FAIMS CV spectrum is a function of several parameters that include solvent composition, pH, and FAIMS instrumental variables such as DV, gas composition, gas temperature and gas pressure. Consequently, a multitude of different "fingerprint" type spectra may be obtained by varying the conditions under which the CV spectra are obtained. These "fingerprint" CV spectra differ from each other because the experimental conditions serve to enhance or modify the separations of various conformers of the protein. For example, if two of the conformers cannot be separated using a carrier gas containing pure nitrogen, but can be separated when the carrier gas is, for example, a 50/50 (v/v) mixture of nitrogen and helium, then the spectra collected in both gas compositions are complimentary. By having multiple reference spectra, collected under several experimental conditions, for various charge states of a protein, a comparison among CV spectra to detect variants is possible.

In another example, a protein sample obtained from a healthy individual is analyzed with the FAIMS device using two solutions, one containing acetic acid, as described supra, and one without acetic acid, for example the solution contains 1 mM ammonium acetate instead of 1% acetic acid. The change in the pH of the solution can be used to affect the conformation of the protein, and thereby changing the appearance of the CV spectra. For example, with cytochrome c, a solution containing 1% acetic acid favors the formation of higher charge states and elongated conformers, compared with a solution containing 1 mM ammonium acetate and no acid, which favors the formation of lower charge states and more compact conformers, with the other solution conditions being equal. By obtaining reference CV spectra for these two conditions, a larger number of conformers of the protein can be separated from each other, or enhanced for detection, and therefore can be used for comparison. Thus, during screening of a protein, characteristic changes, such as for example detection of a previously undetected conformer, may show up in the CV spectrum obtained with one set of solution conditions that indicate a variant that may lead to a diseased state. Another variant of the protein that may also lead to a diseased state may not show characteristic peaks in the CV spectrum using these conditions. Instead, the CV spectra for this variant may only show characteristic changes in the CV spectra obtained with the other set of solution conditions. The experimental conditions will be modified and the spectra evaluated to maximize the number of individual conformers that can be isolated as identifiable peaks in the CV spectrum, and the conditions selected that highlight the particular individual conformers that can be associated with the features, for example a diseased state of the individual, that are required. This example is used to show that by accessing additional gas-phase conformations using different solutions, screening of proteins is facilitated. Optionally, the effectiveness of this procedure to screen individuals is checked, and validated, using other known conventional methods of detection of the disease in the individuals being tested.

Advantageously, the instant invention supports a method for screening protein samples for differences among protein variants without requiring any knowledge as to how the peaks in the CV spectra relate to the conformation of the protein in solution. That is, a change in the CV spectrum of a charge state indicates a change in the conformation of the gas-phase ion but does not necessary indicate how the function of the protein will be affected in solution. Nevertheless, it is possible that characteristic peaks exist in the CV spectrum that can be used as indicators of how the protein will function in solution. As the understanding of the FAIMS techniques improves, specific information regarding the structure of the protein in solution may become available.

Of course, in the above examples a mass spectrometer could be used to detect a difference among the variants in which at least one amino acid is replaced by another amino acid having a different molecular weight. However, the separation mechanisms of the mass spectrometer and the FAIMS device are very different. Since the mass spectrometer is limited to detecting the mass-to-charge ratio of an ion, mass spectrometry detection would not reveal a situation in which only the order of amino acids in the primary sequence has changed. However, the FAIMS device is applicable in this type of example if the modification of the primary sequence leads to a change in the corresponding CV spectrum. In addition, a change in the primary sequence by the replacement of one amino acid with another of different mass may not result in a diseased state. Accordingly, mass spectrometry detection alone would not be able to give meaningful results since only a change in the m/z ratio can be detected and not a change in conformation, which relates to the function of a protein, of a given charge state. Since the FAIMS device is capable of detecting changes in the 3-dimensional structures of gas-phase ions, it may be possible to use certain characteristic features in comparing the CV spectra to determine whether the change in the primary sequence of the protein may lead to a diseased state. For example, during screening of a variant, the appearance of a peak in the CV spectrum of the variant at acertain CV value, which peak is not in the CV spectrum of the protein of a "healthy" individual, may be used to indicate a diseased state. Conversely, the absence of a particular peak in the CV spectrum of the variant at a specified CV value may be indicative of a protein that may lead to a diseased state. For some proteins, a series or a combination of additional and/or missing peaks in the CV spectrum of the various charge state ions of a protein may be required to indicate if the protein will lead to a diseased state.

Numerous other embodiments may be envisaged without departing from the spirit and scope of the invention.

What is claimed is:

1. A method for distinguishing between protein variants, comprising the steps of:
   a) using the same solution conditions, preparing separate solutions for a predetermined protein and for an analyte protein, the analyte protein being a potential variant of the predetermined protein;
   b) obtaining a FAIMS spectrum for each one of the separate solutions by varying a compensation voltage (CV) that is applied to an electrode of the FAIMS so as to obtain, using mass spectrometric ion detection, a fingerprint CV spectrum for each one of the predetermined protein and the analyte protein;
   c) comparing the fingerprint CV spectrum for the predetermined protein to the fingerprint CV spectrum for the analyte protein; and,
   d) registering the analyte protein as a variant of the predetermined protein if the fingerprint CV spectra differ by more than a threshold amount.

2. A method according to claim 1, comprising changing in parallel the solution conditions for the predetermined protein and for the analyte protein so as to obtain other solutions, and further comprising repeating step b) using the other solutions so as to obtain different fingerprint CV spectra for the predetermined protein and for the analyte protein, step c) comparing the different fingerprint CV spectra for the predetermined protein and the analyte protein, and step d) registering the analyte protein as a variant of the predetermined protein based on a result of the comparison between the fingerprint CV spectra in combination with a result of the comparison between the different fingerprint CV spectra.

3. A method according to claim 1, wherein a primary sequence of amino acids of the variant differs from a primary sequence of amino acids of the predetermined protein at a number of amino acid positions that is small relative to the total number of amino acid positions in either primary sequence.

4. A method according to claim 3, wherein the primary sequences of the variant and of the predetermined protein differ at less than five percent of the total number of amino acid positions.

5. A method according to claim 1, wherein the variant of the predetermined protein is associated with an existence of a diseased state in an organism from which the analyte protein was obtained.

6. A method according to claim 1, wherein the predetermined protein is a first reference protein sample that is known to be a normal form of a given protein molecule, and wherein the analyte protein is a second reference protein sample that is known to be a variant form of the given protein molecule.

7. A method according to claim 1, comprising a step of comparing a fingerprint CV spectrum relating to a second analyte protein to the fingerprint CV spectrum relating to the analyte protein.

8. A method according to claim 7, comprising a step of registering the second analyte protein as a same variant of the predetermined protein if the fingerprint CV spectrum of the second analyte protein is substantially identical to the fingerprint CV spectrum of the analyte protein.

9. A method for distinguishing between protein variants, comprising the steps of:
provided a high Field Asymmetric waveform Ion Mobility Spectrometer (FAIMS) analyzer comprising a FAIMS analyzer region defined by a space between two spaced-apart electrodes;
using known solution conditions, preparing a solution including an analyte protein, the analyte protein being a potential variant of a predetermined protein;
producing ions of the analyte protein from the solution including the analyte protein, the ions of the analyte protein for introduction into the FAIMS analyzer region;
using a mass spectrometer, detecting an intensity of the ions of the analyte protein that are transmitted through the FAIMS analyzer region at a predetermined compensation voltage (CV) value and under known FAIMS operating conditions;
determining a difference between the detected intensity and a reference value, the reference value relating to an expected intensity at the predetermined CV value for a normal form of the predetermined protein under the same known solution conditions and under the same known FAIMS operating conditions; and,
registering the analyte protein as a variant of the predetermined protein in dependence upon the determined difference.

10. A method according to claim 9, wherein at least one of the known FAIMS operating conditions and the known solution conditions is selected for providing a plurality of different conformers of the ions of the analyte protein that are transmitted through the FAIMS analyzer region.

11. A method according to claim 10, wherein the at least one of the known FAIMS operating conditions and the known solution conditions is selected for maximizing a number of different conformers of the ions of the analyte protein that are transmitted through the FAIMS analyzer region.

12. A method according to claim 9, wherein the step of detecting an intensity of the ions of the analyte protein includes a step of obtaining a fingerprint CV spectrum for the analyte protein over a range of different CV values.

13. A method according to claim 9, wherein the step of detecting an intensity of the ions of the analyte protein is performed at a single predetermined CV value.

14. A method according to claim 9, wherein the step of detecting an intensity of the ions of the analyte protein is performed at each one of a plurality of different selected CV values.

15. A method according to claim 9, wherein the normal form of the predetermined protein is associated with other than a diseased state in an organism from which the analyte protein was obtained.

16. A method according to claim 9, wherein the step of registering the analyte protein as a variant of the predetermined protein includes a step of providing a human intelligible indication that is indicative of the analyte protein being registered as a variant of the predetermined protein.

* * * * *